US006833389B2

(12) United States Patent
Colombo et al.

(10) Patent No.: US 6,833,389 B2
(45) Date of Patent: Dec. 21, 2004

(54) USE OF THIAMPHENICOL AND DERIVATIVES THEREOF FOR THE PREPARATION OF PHARMACEUTICAL COMPOSITIONS USEFUL IN THE TREATMENT OF *CHLAMYDIA PNEUMONIAE* INFECTIONS

(75) Inventors: Giovanni Battista Colombo, Cassina De Pecchi (IT); Domenico Ungheri, Parabiago (IT); Luciano Licciardello, Monza (IT); Maria Rita Gismondo, Sagittario Milanodue (IT); Lorenzo Drago, Milan (IT)

(73) Assignee: Zambon Group S.p.A., Vicenza (IT)

( * ) Notice: Subject to any disclaimer, the term of this patent is extended or adjusted under 35 U.S.C. 154(b) by 130 days.

(21) Appl. No.: 09/926,738

(22) PCT Filed: Apr. 2, 2001

(86) PCT No.: PCT/EP01/03709

§ 371 (c)(1),
(2), (4) Date: Dec. 11, 2001

(87) PCT Pub. No.: WO01/76585

PCT Pub. Date: Oct. 18, 2001

(65) Prior Publication Data

US 2003/0100614 A1 May 29, 2003

(30) Foreign Application Priority Data

Apr. 11, 2000 (IT) ..................................... MI2000A0776

(51) Int. Cl.⁷ ......................... A61K 31/16; A61K 31/65; A61K 31/43; A61K 31/47
(52) U.S. Cl. ....................... 514/628; 514/152; 514/199; 514/311; 514/826
(58) Field of Search ................................ 514/628, 152, 514/199

(56) References Cited

U.S. PATENT DOCUMENTS 3,691,229 A * 9/1972 Della Bella et al. ..... 260/481 R
6,589,993 B2 * 7/2003 Ungheri et al. ............. 514/628

FOREIGN PATENT DOCUMENTS

WO 00 01378 1/2000

OTHER PUBLICATIONS

Budavari et al., The Merck Index, Twelfth Edition (1996), pp. 1587, abstract No. 9436.*
Jack M. Bernstein, MD, "Treatment of Community–Acquired Pneumonia—IDSA Guidelines," Chest/115/3/Mar., 1999.
Murat V. Kalayoglu, MD, PhD, et al., "*Chlamydia pneumoniae* as an Emerging Risk Factor in Cardiovascular Disease," American Medical Association, JAMA, vol. 288, No. 21, Dec. 4, 2002.
L. Richaldl, et al., "Macrolldes for chronic asthma," The Cochrane Library 2003, Issue 1, pp. 1–16.
"Practice guidelines for the management of community–acquired pneumonia in adults," Bibliographic Source(s)—Bartlett JG, et al., Clin Infect Dis 2000 Aug.; 31 (2), pp. 1–10.
Alessandra Lombardi et al.; "Antimicrobial activity of thiamphenicol–gycinate–acetylcysteinate and other drugs against Chlamydia pneumoniae" Arzeimittel–Forschung, vol. 51, No. 3, pp. 264–267, 2001.
F. Blasi: "Clinical features of chlamydia pneumoniae acute respiratory infection" Clinical Microbiology and Infection, vol. 1, pp. s14–s18, Mar. 1, 1996.

* cited by examiner

*Primary Examiner*—Kevin E. Weddington
(74) *Attorney, Agent, or Firm*—Oblon, Spivak, McClelland, Maier & Neustadt, P.C.

(57) ABSTRACT

Use of thiamphenicol and derivatives thereof for the preparation of pharmaceutical compositions useful for the treatment *Chlamydia pneumoniae* infections is described.

32 Claims, No Drawings

USE OF THIAMPHENICOL AND DERIVATIVES THEREOF FOR THE PREPARATION OF PHARMACEUTICAL COMPOSITIONS USEFUL IN THE TREATMENT OF CHLAMYDIA PNEUMONIAE INFECTIONS

The present invention relates to the use of thiamphenicol and derivatives thereof for the preparation of pharmaceutical compositions useful in the treatment of Chlamydia pneumoniae infections.

Chlamydia pneumoniae is an intracellular bacterium recently considered responsible of respiratory infections both of the upper tract and the lower tract.

This bacterium is one of the most widespread human pathogens and primary infections in children from 5 to 14 years have been supported by documentary evidence. In children the infection is generally mild and asymptomatic, but can be more serious in adult and elderly. Chlamydia pneumoniae is responsible for about 10% of cases of atypical pneumonia and of 5% of cases of bronchitis. It has also been associated with respiratory airways diseases and with new onset asthma and asthmatic bronchitis in the adults. Sinusitis caused by Chlamydia pneumoniae also associated with infections of the lower respiratory tract has been described and, moreover, Chlamydia pneumoniae has been isolated from middle ear fluids of patients with otitis media.

For a survey of the pathologies associated to Chlamydia pneumoniae infections see F. Blasi, Clinical Microbiology and Infections, vol. 1, Suppl. 1, March 1996, S14–S18.

Among the antibiotics more commonly used in therapy, azithromycin and, in particular, clarithromycin resulted active in vitro against Chlamydia pneumoniae and others agents involved in these infections and therefore they are potential therapeutical agents in the treatment of Chlamydia pneumoniae infections.

Some quinolonic antibiotics too, offer a potential therapy for Chlamydia pneumoniae infections.

In the cases of Chlamydia pneumoniae infection the antibiotic treatment can require a long period and cases of Chlamydia pneumoniae chronic persistent infections in which the antibiotic therapy has failed have already been reported.

The restricted number of antibiotics useful in the treatment of Chlamydia pneumoniae infections and the increasing importance that these infections are assuming from a clinical point of view, make necessary the identifying of antibiotics active against Chlamydia pneumoniae. Thiamphenicol (The Merck Index, XII ed., No. 9436, page 1587) is a known antibiotic used for the treatment of Gram-positive and Gram-negative bacterial infection. In the treatment of respiratory pathologies thiamphenicol is often used as glycinate hydrochloride or acetylcysteinate, i.e. an ester of thiamphenicol salified with hydrochloric acid or with acetylcysteine respectively.

To our knowledge no data concerning the activity of thiamphenicol or derivatives thereof versus Chlamydia pneumoniae is reported in the literature. It is known instead that thiamphenicol is active against Chlamydia trachomatis, a pathogen responsible of urogenital apparatus infections, but its activity is markedly lower than that of other antibiotics, such as for example erythromycin [G. Ridgeway et al., J. Antimicrob. Chemother. (1979), 5(4), 483–4]. We have now found that thiamphenicol is particularly effective in the treatment of infections caused by Chlamydia pneumoniae.

It is therefore an object of the present invention the use of thiamphenicol and derivatives thereof for the preparation of a pharmaceutical compositions useful in the treatment of Chlamydia pneumoniae infections.

The pharmaceutical compositions useful in the present invention are compositions for enteral or parenteral use containing thiamphenicol or derivatives thereof such as, for example, thiamphenicol glycinate and salts thereof.

Particularly preferred is the use of thiamphenicol glycinate acetylcysteinate.

Also preferred is the use of thiamphenicol glycinate hydrochloride.

The amount of active ingredient, expressed as thiamphenicol, contained in the pharmaceutical composition may change depending on the administration way and on the seriousness of the infection but is generally comprised between 250 mg and 5000 mg per dose, more preferably between 500 mg and 2000 mg.

The pharmaceutical compositions can be in a solid or liquid form, suitable for administering by injectable, oral or aerosol route.

Preferred are the pharmaceutical compositions suitable for administering by aerosol or injectable route.

More preferred are the pharmaceutical compositions suitable for administering by aerosol or injectable route containing thiamphenicol glycinate hydrochloride or acetylcysteinate.

Particularly suitable are the pharmaceutical compositions already on the market with the trademark FLUIMUCIL ANTIBIOTICO® and GLITISOL®.

The thiamphenicol efficacy against strains of Chlamydia pneumoniae of recent clinical isolation has been demonstrated in vitro by calculating the MIC (Minimum Inhibitory Concentration) in comparison with other antibiotics. It is important to underline as thiamphenicol showed a MIC completely comparable, or better, with respect to that of reference antibiotics already used in therapy for the treatment of Chlamydia pneumoniae infections.

With the aim to better illustrate the present invention the following example is now given.

MATERIAL AND METHODS

Chlamydia pneumoniae Strains

Chlamydia pneumoniae TW183 and Chlamydia pneumoniae 2023 were obtained from American Type Culture Collection. The other strains (No. 9 isolated) were clinically isolated in the period 1997–1999.

Antibiotics

The following antibiotics were used: thiamphenicol glycinate acetylcysteinate (TGA), azithromycin, ciprofloxacin, ceftriaxone, amoxicillin, clarithromycin, doxycycline and tetracycline hydrochloride.

Cell Cultures

Monolayers of Hep-2 cells were prepared by seeding $2 \times 10^5$ cell/ml in EMEM with 10% fetal calf serum supplemented with L-glutammine, on 12 mm cover slips and left at 35° C., 5% $CO_2$ for 24 to 48 hours for confluent growth. The growth medium was removed and Hep-2 monolayers were inoculated with the different strains at predetermined concentration calculated to give $3–5 \times 10^2$ inclusions for well.

The monolayers, inoculated with Chlamydia pneumoniae were centrifuged at 1700 g for 60 minutes at 30° C.

Supernatant was removed and was replaced with 2.0 ml of EMEM containing 2% fetal calf serum, L-glutammine, cycloheximide 1 $\mu$g/ml and different dilutions of the tested antibiotics.

In positive control no antibiotic was added and negative control were considered wells not inoculated with Chlamydia pneumoniae.

Cells were incubated at 35° C. in atmosphere additionated with 5% $CO_2$, for 3 days, then the monolayers were fixed with acetone for 10 minutes at −20° C. and stained with a fluorescein-coniugated antibody specific for *Chlamydia pneumoniae* (Argene Biosoft) and observed under a fluorescence microscope.

All tests were run in duplicate. The number of inclusions were counted and the MIC (the lowest concentration at which complete inhibition of inclusion formation was observed) was determined.

Results

The activities of the tested antibiotics are shown in table 1.

TABLE 1

Antimicrobic activity in vitro against stains of *Chlamydia pneumoniae*

| ANTIBIOTIC | MIC (μg/ml) |
|---|---|
| Clarithromycin | 0.03–0.25 |
| Azithromycin | 0.06–0.5 |
| Amoxicillin | >16 |
| Doxycycline | 0.06–0.25 |
| Ciprofloxacin | 0.5–2 |
| Ceftriaxone | >16 |
| Tetracycline | 0.06–0.5 |
| TGA | 0.03–0.25 |

Clarithromycin and thiamphenicol glycinate acetylcysteinate (TGA) are the most active antibiotics (MIC range 0.03 and 0.25 μg/ml for both).

In table 2 the MIC values per strain of each test are shown.

TABLE 2

| strain | Clarithromycin | | azithromycin | | Doxycycline | | ciprofloxacin | | Tetracycline | | TGA | |
|---|---|---|---|---|---|---|---|---|---|---|---|---|
| | I | II | I | II | I | II | I | II | I | II | I | II |
| | μg/ml | | μg/ml | | μg/ml | | μg/ml | | μg/ml | | μg/ml | |
| 1 | 0.03 | 0.03 | 0.5 | 0.125 | 0.06 | 0.125 | 1 | 1 | 0.06 | 0.06 | 0.03 | 0.06 |
| 2 | 0.25 | 0.03 | 0.06 | 0.25 | 0.125 | 0.125 | 0.5 | 2 | 0.06 | 0.06 | 0.03 | 0.03 |
| 3 | 0.03 | 0.03 | 0.06 | 0.06 | 0.125 | 0.125 | 0.5 | 1 | 0.125 | 0.125 | 0.125 | 0.125 |
| 4 | 0.125 | 0.06 | 0.5 | 0.5 | 0.06 | 0.06 | 1 | 1 | 0.125 | 0.5 | 0.25 | 0.06 |
| 5 | 0.03 | 0.03 | 0.25 | 0.25 | 0.125 | 0.06 | 0.5 | 0.5 | 0.125 | 0.25 | 0.125 | 0.125 |
| 6 | 0.03 | 0.125 | 0.125 | 0.25 | 0.06 | 0.06 | 2 | 2 | 0.06 | 0.5 | 0.03 | 0.03 |
| 7 | 0.125 | 0.125 | 0.25 | 0.25 | 0.06 | 0.06 | 2 | 1 | 0.125 | 0.125 | 0.03 | 0.03 |
| 8 | 0.125 | 0.125 | 0.25 | 0.25 | 0.25 | 0.06 | 0.5 | 2 | 0.06 | 0.06 | 0.125 | 0.03 |
| 9 | 0.125 | 0.03 | 0.5 | 0.125 | 0.25 | 0.25 | 0.5 | 0.5 | 0.06 | 0.5 | 0.125 | 0.125 |
| ATCC 2023 | 0.03 | 0.03 | 0.06 | 0.125 | 0.06 | 0.06 | 0.5 | 0.5 | 0.06 | 0.125 | 0.03 | 0.03 |
| TW 183 | 0.03 | 0.125 | 0.125 | 0.25 | 0.125 | 0.25 | 0.5 | 1 | 0.06 | 0.06 | 0.06 | 0.03 |

All the values are under the break point (thiamphenicol≦16 μg/ml, clarithromycin≦2 μg/ml, amoxicillin≦2 μg/ml, doxycycline≦4 μg/ml, ciprofloxacin≦1 μg/ml, tetracycline≦2 μg/ml) except for azithromycin (≦1 μg/ml) and ceftriaxone (≦2 μg/ml).

Moreover thiamphenicol has shown the best value of the ratio between MIC (0.03–0.25 μg/ml) and break point (≦16 μg/ml) in comparison with the others antimicrobial compounds the break point values of which are lower than thiamphenicol.

What is claimed is:

1. A composition comprising:
   one or more compounds selected from the group consisting of thiamphenicol and a thiamphenicol derivative(s) in a form and in a dosage suitable for treatment of a *Chlamydia pneumoniae* infection, and one or more other antibiotic(s) active against *Chlamydia pneumoniae*.

2. The composition of claim 1 that comprises thiamphenicol glycinate or a salt of thiamphenicol glycinate.

3. The composition of claim 1 that comprises thiamphenicol glycinate acetylcysteinate.

4. The composition of claim 1 that comprises thiamphenicol glycinate hydrochloride.

5. The composition of claim 1, comprising one or more quinolonic antibiotic(s) active against *Chlamydia pneumoniae*.

6. The composition of claim 1 in a form suitable for parenteral administration.

7. The composition of claim 1 in a form suitable for injection.

8. The composition of claim 1 in a form suitable for oral administration.

9. The composition of claim 1 in a form suitable for aerosol administration.

10. A method for treating a subject having a *Chlamydia pneumoniae* infection comprising;
    administering an effective amount of one or more compound(s) selected from the group consisting of thiamphenicol and a thimphenicol derivative(s).

11. The method of claim 10 that comprises administering thiamphenicol glycinate or a salt of thiamphenicol glycinate.

12. The method of claim 10 that comprises administering thiamphenicol glycinate acetylcysteinate.

13. The method of claim 10 that comprises administering thiamphenicol glycinate hydrochloride.

14. The method of claim 10, further comprising administering one or more other antibiotic(s) active against *Chlamydia pneumoniae*.

15. The method of claim 10 that comprises administering thiamphenicol or a thiamphenicol derivative parenterally.

16. The method of claim 10 that comprises administering thiamphenicol or a thiamphenicol derivative as an injection.

17. The method of claim 10 that comprises administering thiamphenicol or a thiamphenicol derivative orally.

18. The method of claim 10 that comprises administering thiamphenicol or a thiamphenicol derivative as an aerosol.

19. The method of claim 10, wherein said subject has a respiratory infection.

20. The method of claim 10, wherein said subject has a a typical pneumonia or bronchitis.

21. The method of claim 10, wherein said subject has asthma or asthmatic bronchitis.

22. The method of claim 10, wherein said subject has sinusitis.

23. The method of claim 10, wherein said subject has an ear infection or otitis media.

24. The method of claim 10, wherein said subject is a human.

25. The method of claim 10, comprising administering a dose of thiamphenicol or a thiamphenicol derivative ranging from 250 mg to 5000 mg.

26. The method of claim 10, comprising administering a dose of thiamphemcol or a thiamphenicol derivative ranging from 500 mg to 2000 mg.

27. A method for inhibiting the growth of *Chlamydia pneumonia* comprising contacting *Chlamydia pneumonia* or a cell comprising *Chlamydia pneumonia* with thiamphenicol or a thiamphenicol derivative.

28. The method of claim 27 comprising contacting *Chlamydia pneumonia* or a cell comprising *Chlamydia pneumonia* with a concentration of at least 0.03 µg/ml of thiamphenicol or a thiamphenicol derivative.

29. The method of claim 27 comprising contacting *Chlamydia pneumonia* or a cell comprising *Chlamydia pneumonia* with a concentration of at least 0.25 µg/ml of thiamphenicol or a thiamphenicol derivative.

30. The method of claim 27 comprising contacting *Chlamydia pneumonia* or a cell comprising *Chlamydia pneumonia* with a concentration ranging from 0.03 µg/ml to 0.125 µg/ml of thiamphenicol or a thiamphenicol derivative.

31. The composition of claim 1, which comprises one or more antibiotics selected from the group consisting clarithromycin, azithromycin, amoxicillin, deoxycycline, ciprofloxacin, ceftriaxone, and tetracycline.

32. The method of claim 10, comprising administering a composition, which comprises one or more antibiotics selected from the group consisting clarithromycin, azithromycin, amoxicillin, deoxycycline, ciprofloxacin, ceftriaxone, and tetracycline.

* * * * *